United States Patent [19]

Rikukawa et al.

[11] 3,971,951

[45] July 27, 1976

[54] APPARATUS FOR MEASURING TWO DIFFERENT FLUORESCENCES OF A SAMPLE

[75] Inventors: Katsuji Rikukawa, Tokyo; Kenji Onogi, Chigasaki, both of Japan

[73] Assignee: Nippon Kogaku K.K., Tokyo, Japan

[22] Filed: Oct. 10, 1974

[21] Appl. No.: 513,869

[30] Foreign Application Priority Data

Oct. 17, 1973  Japan.............................. 48-115687

[52] U.S. Cl. .............................. 250/458; 250/461 B
[51] Int. Cl.² .......................................... G01J 1/58
[58] Field of Search .......... 250/302, 304, 458, 459, 250/461

[56] References Cited
UNITED STATES PATENTS

| 3,825,762 | 7/1974 | White | 250/458 |
| 3,832,555 | 8/1974 | Ohnishi | 250/461 X |

*Primary Examiner*—Archie R. Borchelt
*Attorney, Agent, or Firm*—Shapiro and Shapiro

[57] ABSTRACT

In apparatus, such as a fluorometric microscope, for measuring two different fluorescences in a sample, the sample is irradiated by light modulated at a first frequency and having a first wavelength for causing a first fluorescence and also is irradiated by light modulated at a second frequency different from the first frequency and having a second wavelength for causing a second fluorescence. A photoelectric element is responsive to the light emitted by the sample during both fluorescences for generating an electrical signal representative of the combined intensities of the two fluorescences. From this electrical signal, a demodulator derives first and second signal components having the first and second frequencies, respectively, and having amplitudes representative of the individual intensities of the first and second fluorescences, respectively.

9 Claims, 1 Drawing Figure

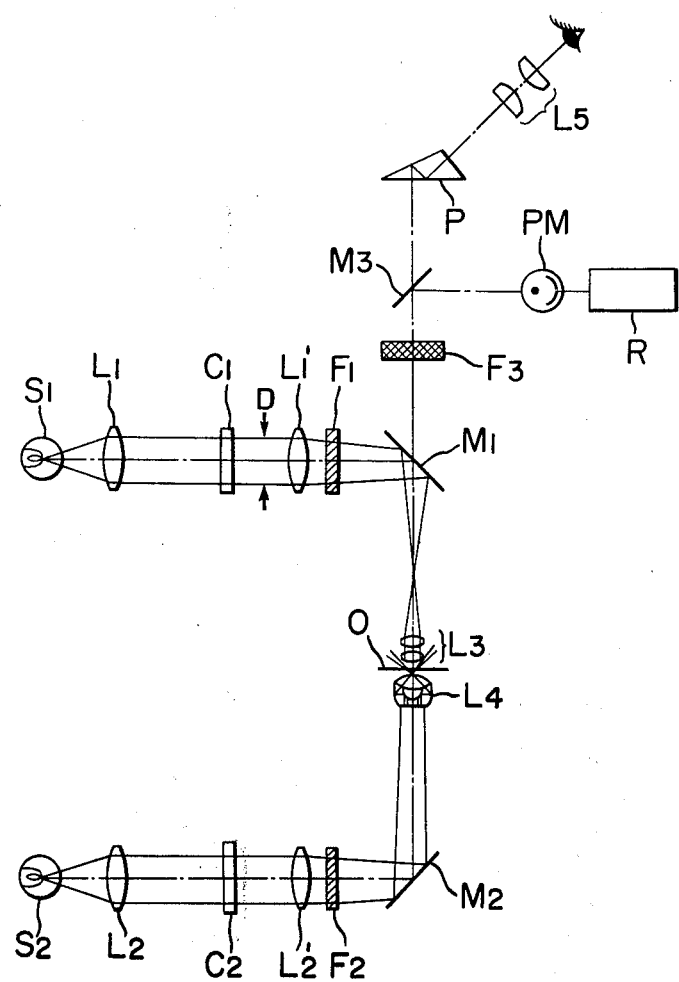

APPARATUS FOR MEASURING TWO DIFFERENT FLUORESCENCES OF A SAMPLE

BACKGROUND OF THE INVENTION

1. Field of the Invention

This invention relates to fluorometric apparatus, and, more particularly, to apparatus for measuring two different fluorescent substances in a sample.

2. Description of the Prior Art

In its broad sense, "fluorescence" is a phenomenon wherein a substance absorbs ultraviolet rays or other light energy having short wavelength and produces light having a longer wavelength than the absorbed wavelength. A fluorescence microscope is an instrument which utilizes the phenomenon of fluorescence to observe and analyze living cells and other structures.

Nearly all substances are naturally fluorescent to some degree when irradiated with light energy of short wavelength. However, there are certain substances, such as proteins and carbohydrates, which are not fluorescent. Such non-fluorescing substances may be made to fluoresce by dyeing or staining them with a fluorescent substance called a fluorochrome or by employing the fluorescence antibody technique which utilizes the property of antibody molecules of combining with fluorochromes. In some cases, the non-fluorescent substances are stained with two different fluorochromes in the technique known as double staining.

The constituents of samples, such as cells or other structures, which fluoresce either naturally or by the addition of fluorochromes, may be determined by measuring the amount of fluorescent substance contained in the sample. In the technique of fluorescence photometry, for example, the constituents of a sample can be determined by a single metering step when the sample has a single natural fluorescence or after it has been dyed with a single fluorescent substance or fluorochrome. However, in cases where the sample has two different natural fluorescences or where the sample has been stained with two different fluorescent substances or fluorochromes (double staining), it is necessary to employ a highly efficient excitation lamp for irradiating the sample to cause both fluorescences to occur simultaneously and then to measure the emitted light corresponding to each individual fluorescence. Unfortunately, this measurement technique is not desirable for preventing fading of the sample. Consequently, each of the measuring steps must be done very quickly, making measurement extremely difficult. Thus, in order to avoid making errors in the measurements, the operator must have a high degree of skill.

To avoid the need for individually measuring the emitted light corresponding to two simultaneously occurring fluorescences, two excitation lamps may be employed to separately irradiate the sample to cause the fluorescences to occur at different times. If the sample were irradiated by both lamps simultaneously, it would be difficult to distinguish the light emitted during the fluorescences from the light produced by the excitation lamps. For example, in some cases, the wavelength of the light emitted during one or both of the fluorescences may be very close to the wavelength of one of the excitation lamps so that it is difficult to separate the light of the excitation lamp from the emitted light. Thus, the light from the excitation lamp, which is stronger than the emitted light, would mix into the viewing system and the measuring system, making it impossible either to view or to measure the intensities of the two fluorescences.

SUMMARY OF THE INVENTION

Accordingly, an object of the invention is to provide improved fluorometric apparatus which enables simultaneous measurement of two different fluorescences of a sample and which has none of the above-noted disadvantages.

Fluorometric apparatus constructed in accordance with the invention comprises a first irradiating system for irradiating the sample with light modulated at a first frequency and having a first wavelength for causing a first fluorescence, a second irradiating system for irradiating the sample with light modulated at a second frequency different from the first frequency and having a second wavelength comprising a second fluorescence, and detector means, such as a photoelectric element and a demodulator, responsive to light emitted during both fluorescences for detecting the respective individual intensities of the two fluorescences.

In the preferred embodiment, the first irradiating system includes a dichroic mirror for directing the modulated light having the first wavelength, which is preferably longer than the second wavelength, onto the sample and for permitting the emitted light corresponding to both fluorescences to pass therethrough to reach the detecting means. The first irradiating system also includes an objective lens for focusing the light onto the sample, the objective lens having a non-reflective coating thereon to reduce reflection of the light back toward the detecting means. An absorbing filter may be employed to prevent the light of the irradiating systems from reaching the detecting means. The second irradiating system includes a dark field condenser lens for directing the light having the second wavelength onto the sample. Each irradiating system includes a source of light, a chopper for modulating the light, and a filter for passing the appropriate wavelength. A viewing optical system may include an eyepiece and a seme-transparent mirror which splits the light emitted during fluorescence into first and second components which are directed to the detecting means and into the eyepiece, respectively.

BRIEF DESCRIPTION OF THE DRAWING

The single FIGURE of the drawing is a schematic view illustrating the preferred embodiment of the fluorometric apparatus made in accordance with the invention.

DESCRIPTION OF THE PREFERRED EMBODIMENT

Referring to the drawing, S1 designates a light source, which may comprise a high pressure mercury lamp or the like, and C1 designates a chopper for modulating the light from source S1 at frequency $f1$. The chopper may comprise any suitable light-modulating device of known construction, such as a mechanical, electro-mechanical or electro-optical light modulator. Lenses L1 and L1' provide a parallel optical system in which chopper C1 is disposed. D denotes a diaphragm for limiting the cross-sectional area of the light beam provided by the optical system.

F1 designates a narrow-band-pass filter disposed in the path of the modulated light beam for passing only light having a predetermined wavelength $\lambda 1$, which is selected to excite a constituent of the sample to be analyzed to a first fluorescence to emit light having a longer wavelength $\lambda 1'$. M1 is a dichroic mirror for reflecting light having wavelengths equal to or shorter than wavelength $\lambda 1$ and for passing therethrough light having wavelengths longer than $\lambda 1$, which includes the light emitted during both fluorescences. L3 is an objective lens. The path of the excitation light, which is modulated at frequency $f1$ and which has wavelength $\lambda 1$, is changed 90° by dichroic mirror M1 so that the light passes through the objective L3 to irradiate the sample (not shown) which is supported on a stage O. The elements just described constitute an incident irradiating optical system.

S2 is a light source similar to light source S1 in the incident irradiating optical system. Lenses L2 and L2' are similar to lenses L1 and L' and provide a parallel optical system. C2 designates a chopper disposed in the parallel optical system. Chopper C2 modulates the light from source S2 at a frequency $f2$ different from the modulation frequency $f1$ produced by chopper C1 in the incident irradiating optical system. F2 is a narrow-band-pass filter disposed in the path of the light modulated by the chopper C2 and passes only light having a predetermined wavelength $\lambda 2$, which is selected to excite a constituent of the sample to a second fluorescence to emit light at a longer wavelength $\lambda 2'$, which is preferably different from wavelength $\lambda 1'$. For reasons which will be apparent later, wavelength $\lambda 2$ provided by filter F2 is shorter than wavelength $\lambda 1$ provided by filter F1. M2 is a mirror and L4 is a dark field condenser. The path of this excitation light, which is modulated at frequency $f2$ and which has wavelength $\lambda 2$, is changed 90° by mirror M2 so that the light passes through the dark field condenser to irradiate the sample on stage O. The elements just described constitute a transmitting irradiating optical system.

A semi-transparent mirror M3 is disposed in the path of the light emitted during both fluorescences (i.e., the light having wavelengths $\lambda 1'$ and $\lambda 2'$) which passes through dichroic mirror M1, mirror M3 splitting the emitted light into two components. A metering optical system comprising a photoelectric element PM and a frequency separation circuit R is responsive to one of the components for detecting the respective individual intensities of the two fluorescences in a manner to be described hereinafter. A viewing optical system comprising a light-path-changing prism P and an eyepiece L5, which may form part of a fluorescence microscope, receives the other component for enabling viewing of the fluorescences. F3 is an absorption filter which removes light other than that having wavelengths $\lambda 1'$ and $\lambda 2'$. Where the dark field condenser L4 comprises a condenser lens having a simple transmission characteristic, the intensity of the excitation light having wavelength $\lambda 2$ would be so great that it could not be completely cut off (i.e., reflected) be the dichroic mirror M1. In such a case, therefore, the absorbing filter F3 is required to absorb any of the light having wavelength $\lambda 2$ which passes through mirror M1. Futhermore, filter F3 is necessary to absorb any light having wavelength $\lambda 1$ which is reflected back toward mirror M1 (for example, by the surface of objective lens L3) and which is not completely cut off by mirror M1.

Operation of the above-described apparatus will now be described. The two constituents to be measured in the sample under study must be fluorescent in response to excitation light having two different wavelengths, referred to hereinabove as wavelengths $\lambda 1$ and $\lambda 2$, respectively. If both constituents are not naturally fluorescent, either one or both of them may be stained by suitable fluorescent substances or fluorochromes to provide the necessary fluorescence. The sample is then placed on stage O for measurement of the two fluorescences. Prior to measurement of the sample, a test plate suitably treated to provide two different fluorescences is placed on the stage for measurement or metering. By comparing the values obtained through fluorescence measurement (hereinafter described) with the known values of the sample, the fluorometric apparatus can be calibrated.

The diverging light rays from source S1 are made parallel by lens L1 and are modulated at a selected frequency $f1$ by chopper C1, wherein the modulated light rays are condensed (i.e., made to converge) by lens L1', which also directs the light toward dichroic mirror M1. Filter F1 blocks all the light rays except those having wavelength $\lambda 1$, thereby forming an excitation light which is directed onto the sample by the objective lens L3. A small percentage of this light is reflected back toward dichroic mirror M1 by the surface of the objective lens and by the finished surfaces of stage O. Substantially all of this reflected light is reflected back toward light source S1 by dichroic mirror M1. The small percentage of the light which passes through dichroic mirror is absorbed by filter F3. When the excitation light impinges upon the sample, the fluorescent substance or fluorochrome which is responsive to wavelength $\lambda 1$ fluoresces, emitting light having wavelength $\lambda 1'$. The emitted light passes through dichroic mirror M1 and filter F3 and strikes semi-transparent mirror M3. The component of light reflected by the mirror is directed onto the photoelectric element PM while the component of light passing through the mirror is directed by prism P into eyepiece L5. Taking the factor of fading into consideration, irradiation of the entire sample by the excitation light should be avoided during metering. Therefore, the field of irradiation of the light is limited to a small spot by means of diaphragm D.

In similar manner, the diverging light rays from source S2 in the transmitting irradiating optical system are made parallel by lens L2, are modulated at frequency $f2$ by chopper C2, whereafter they are condensed by lens L2' and directed toward mirror M2. Filter F2 blocks out all of the light rays except those having wavelength $\lambda 2$, thereby providing an excitation light which is directed onto the sample by the dark field condenser L4 and which then escapes outwardly relative to the objective lens L3, as shown. When this excitation light impinges upon the sample, the fluorescent substance or fluorochrome which is responsive to light having wavelength $\lambda 2$ fluoresces, emitting light having wavelength $\lambda 2'$ which enters the metering and viewing optical system in the same manner as described above with respect to the emitted light having wavelength $\lambda 1'$. Any light which passes through the dichroic mirror M1 other than light having wavelengths $\lambda 1'$ and $\lambda 2'$, such as excitation light reflected by objective lens L3 or scattered by condenser L4, are intercepted by absorbing filter F3 so that the only light which reaches semi-transparent mirror M3 is the light emitted by the sample during the fluorescences.

If the excitation light in the incident or downward irradiation system were selected to have a wavelength $\lambda 1$ shorter than the wavelength $\lambda 2$ of the excitation light in the upward or transmitting irradiation system, so that the wavelength $\lambda 2$ of the upward excitation light were closer than wavelength $\lambda 1$ to the wavelengths $\lambda 1'$ and $\lambda 2'$ of the emitted light, a simple filter would be insufficient to separate the upward excitation light from the emitted light. This is the case because the intensity of the upwardly directed excitation light would have an intensity much greater than the intensity of the emitted light. However, if the excitation light having the longer wavelength were directed downwardly to irradiate the sample, only a small percentage of that excitation light would be reflected back toward the viewing and metering optical systems by the surface of the objective lens L3. Furthermore, it becomes possible to reduce the amount of reflection by applying an anti-reflection coating to the surface of the lens. It will therefore be apparent that, with respect to the viewing and measuring optical systems, the downwardly directed excitation light can be attenuated considerably more than the upwardly directed excitation light. Thus, in the case where one of the excitation lights has a wavelength close to the wavelength of the light emitted during fluorescence, that excitation light should be employed in the incident or downward irradiating optical system and the excitation light having the shorter wavelength should be employed in the upward or transmitting irradiating optical system.

Photoelectric element PM is responsive to the light emitted during both fluorescences (i.e., the light having wavelengths $\lambda 1'$ and $\lambda 2'$) for generating an electrical signal having an amplitude corresponding to the sum of the intensities of the light emitted during both fluorescences. However, because the excitation light for incident and transmitting irradiation is modulated at frequencies $f1$ and $f2$, respectively, the light emitted during the respective fluorescences is also modulated at those frequencies. Thus, from this electrical signal the frequency separation current R, which may comprise a demodulator, can separate first and second component signals having frequencies $f1$ and $f2$, respectively, which represent the respective individual intensities of the two fluorescences. These detected values are then compared with the values measured by the use of the test plate to obtain corrected values thereof.

The light passed into the viewing optical system through semi-transparent mirror M3 is directed toward the eyepiece L5 by prism P to enable the sample and the fluorescences to be viewed.

In the illustrated embodiment, chopper C1 of the incident irradiating optical system is disposed in the parallel optical system. However, alternatively, the chopper may be located at any desired position between the light source S1 and the semi-transparent mirror M1. Similarly, in the transmitting irradiating optical system, the chopper can be located in any position between light source S2 and mirror M2. Furthermore, the filters F1 and F2 do not have to be in the positions shown, but may be placed in any other suitable positions.

The fact that the dark field condenser L4 is employed in the transmitting optical system is advantageous in that it prevents a substantial amount of the excitation light in that system from entering the viewing and the metering optical systems after irradiating the sample. However, the use of the dark field condenser is also disadvantageous with respect to fading because no field stop is introduced into the system. When consideration must be given to fading, metering may be effected with the dark field condenser being replaced by a simple transmission-type condenser and a diaphragm. However, in such a case the excitation light in the transmitting irradiating optical system would then pass directly into the viewing and metering systems, even if the dichroic mirror M1 were effective to reflect almost all of the excitation light toward the light source S1. For this reason, the absorbing filter F3, which is capable of absorbing all of the excitation light passing through the dichroic mirror, is provided between the dichroic mirror and the semi-transparent mirror M3.

Thus, in the fluorometric apparatus constructed in accordance with the invention, incident excitation light and transmitted excitation light are advantageously employed to enable simultaneous measurement of two different fluorescences in a sample, such as a double-stained sample, without the disadvantage of fading.

Furthermore, the transmissivity, reflection factor and other characteristics of the sample may be simultaneously measured merely by replacing the dark field condenser with a simple transmission-type condenser.

It is believed that the advantages and improved results furnished by the fluorometric apparatus of the invention will be apparent from the foregoing description of a preferred embodiment of the invention. Various changes and modifications may be made without departing from the spirit and scope of the invention as sought to be defined in the following claims.

We claim:

1. Fluorometric apparatus for measuring two different fluoroscences of a sample, the apparatus comprising a first illumination optical system for irradiating the sample with a first excitation light modulated at a first frequency and having a first wavelength, the first excitation light being reflected to the sample and the sample emitting a first fluorescent light, a second illumination optical system for irradiating the sample with a second excitation light modulated at a second frequency and having a second wavelength, the second excitation light being transmitted through the sample and the sample emitting a second fluorescent light, filter means for the passage therethrough of the first and second fluorescent lights emitted by the sample and for preventing said excitation lights from passing therethrough, and detecting means responsive to said first and second fluorescent lights passed through said filter means for detecting the individual intensities of the first and second fluorescent lights.

2. Fluorometric apparatus as set forth in claim 1 wherein the detecting means comprises a photoelectric element for generating an electrical signal representative of the light emitted by the first and second fluorescent lights, and means responsive to the electrical signal for deriving therefrom first and second signal components having the first and second frequencies, respectively, and representing the individual intensities of the first and second fluorescent lights, respectively.

3. Fluorometric apparatus as set forth in claim 1, wherein the first illumination optical system includes a dichroic mirror for directing the first excitation light onto the sample and for permitting the second fluorescent light to pass therethrough to reach the detecting means.

4. Fluorometric apparatus as set forth in claim 3, wherein the first wavelength is longer than the second wavelength.

5. Fluorometric apparatus as set forth in claim 4, wherein the first illumination optical system includes an objective lens for directing the light having the first wavelength onto the sample, and wherein the objective lens has an anti-reflection coating thereon for reducing reflection of the light having the first wavelength.

6. Fluorometric apparatus as set forth in claim 1, wherein the second illumination optical system includes a condenser lens for directing the light having the second wavelength onto the sample.

7. Fluorometric apparatus as set forth in claim 6, wherein the condenser lens comprises a dark field condenser lens.

8. Fluorometric apparatus as set forth in claim 1, wherein each illumination optical system comprises a source of light, means for modulating the light at the respective one of the first and second frequencies, and a filter for passing only light having the respective one of the first and second wavelengths.

9. Fluorometric apparatus as set forth in claim 1, further comprising an eyepiece and means for splitting the light of the first and second fluoroescent lights into first and second components which are directed to the detecting means and to the eyepiece, respectively.

* * * * *